US008425585B2

(12) United States Patent
Melsheimer et al.

(10) Patent No.: US 8,425,585 B2
(45) Date of Patent: Apr. 23, 2013

(54) THORACIC ARCH STENT GRAFT AND METHOD OF DELIVERY

(75) Inventors: Jeffry S. Melsheimer, Springville, IN (US); David Ernest Hartley, Subiaco (AU); Michael Lawrence-Brown, City Beach (AU); Gregory Paul Van Schie, Oegstgeest (NL)

(73) Assignee: Cook Medical Technologies LLC, Bloomington, IN (US)

( * ) Notice: Subject to any disclaimer, the term of this patent is extended or adjusted under 35 U.S.C. 154(b) by 1031 days.

(21) Appl. No.: 11/975,950

(22) Filed: Oct. 23, 2007

(65) Prior Publication Data
US 2008/0114445 A1 May 15, 2008

Related U.S. Application Data

(60) Provisional application No. 60/853,914, filed on Oct. 24, 2006, provisional application No. 60/853,915, filed on Oct. 24, 2006.

(51) Int. Cl.
*A61F 2/06* (2006.01)
(52) U.S. Cl.
USPC .................................. 623/1.15; 623/1.13
(58) Field of Classification Search .................. 623/1.1, 623/1.13, 1.16, 1.17, 1.15, 1.22, 1.28, 1.29, 623/1.37, 1.27; 606/191
See application file for complete search history.

(56) References Cited

U.S. PATENT DOCUMENTS

| 4,830,003 | A | * | 5/1989 | Wolff et al. | 606/191 |
|---|---|---|---|---|---|
| 6,071,307 | A | * | 6/2000 | Rhee et al. | 623/1.13 |
| 6,974,471 | B2 | * | 12/2005 | Van Schie et al. | 623/1.12 |
| 7,279,003 | B2 | * | 10/2007 | Berra et al. | 623/1.13 |
| 2002/0052644 | A1 | | 5/2002 | Shaolian et al. | |
| 2004/0106978 | A1 | | 6/2004 | Greenberg et al. | |
| 2004/0186560 | A1 | * | 9/2004 | Alt | 623/1.35 |
| 2006/0030926 | A1 | * | 2/2006 | Berra | 623/1.13 |
| 2007/0055299 | A1 | * | 3/2007 | Ishimaru et al. | 606/191 |
| 2008/0195191 | A1 | * | 8/2008 | Luo et al. | 623/1.13 |

FOREIGN PATENT DOCUMENTS

| WO | WO 03/034948 A1 | 5/2003 |
|---|---|---|
| WO | WO 2006/125382 A1 | 11/2006 |
| WO | PCT/US2007/022488 | 4/2008 |

OTHER PUBLICATIONS

ISR/PCT/US2007/022488, filed Apr. 14, 2008, EPO.

* cited by examiner

*Primary Examiner* — Thomas J Sweet
*Assistant Examiner* — Matthew Schall
(74) *Attorney, Agent, or Firm* — Richard J. Godlewski

(57) ABSTRACT

A stent arrangement (12) and a stent graft (2) for curved lumens of the body. The stent graft has a tubular body (4) of a graft material, at least a portion of which may be arcuate to define an inner curved side (4*b*) and an outer curved side (4*a*) at least when deployed into the curved vessel. The stent graft has a plurality of self expanding stents (10, 12, 13) affixed thereto with a greater distance (11*a*) between the stents on the outer curved side than on the inner curved side. The stents can be normal, tapered on one or both ends or skewed. When mounted onto a deployment device a twist (152, 154) may be provided in the graft material between adjacent stents to nest the stents.

7 Claims, 14 Drawing Sheets

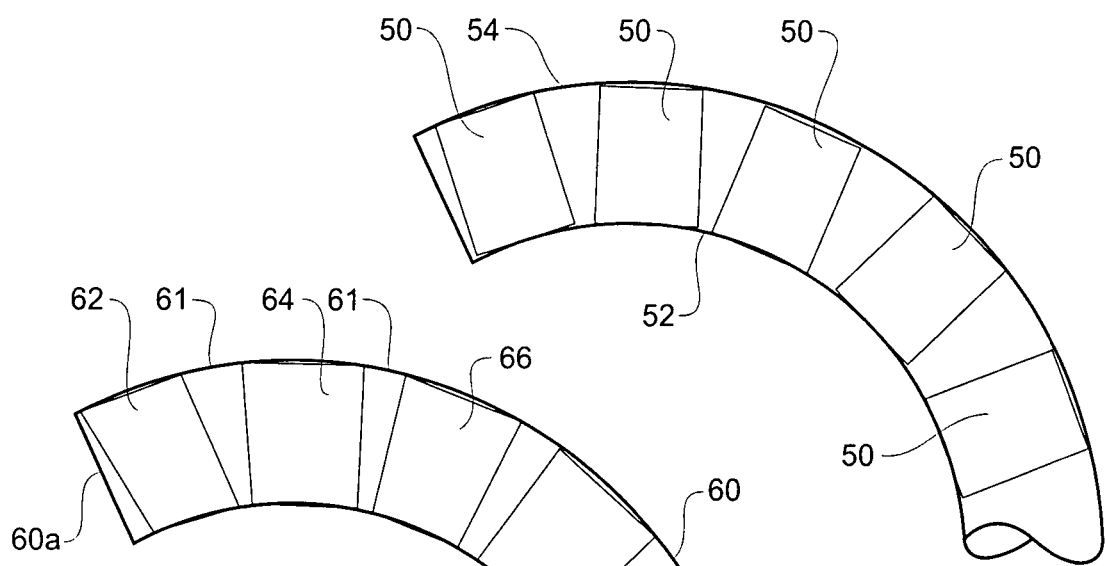
Fig 6A
Fig 6B
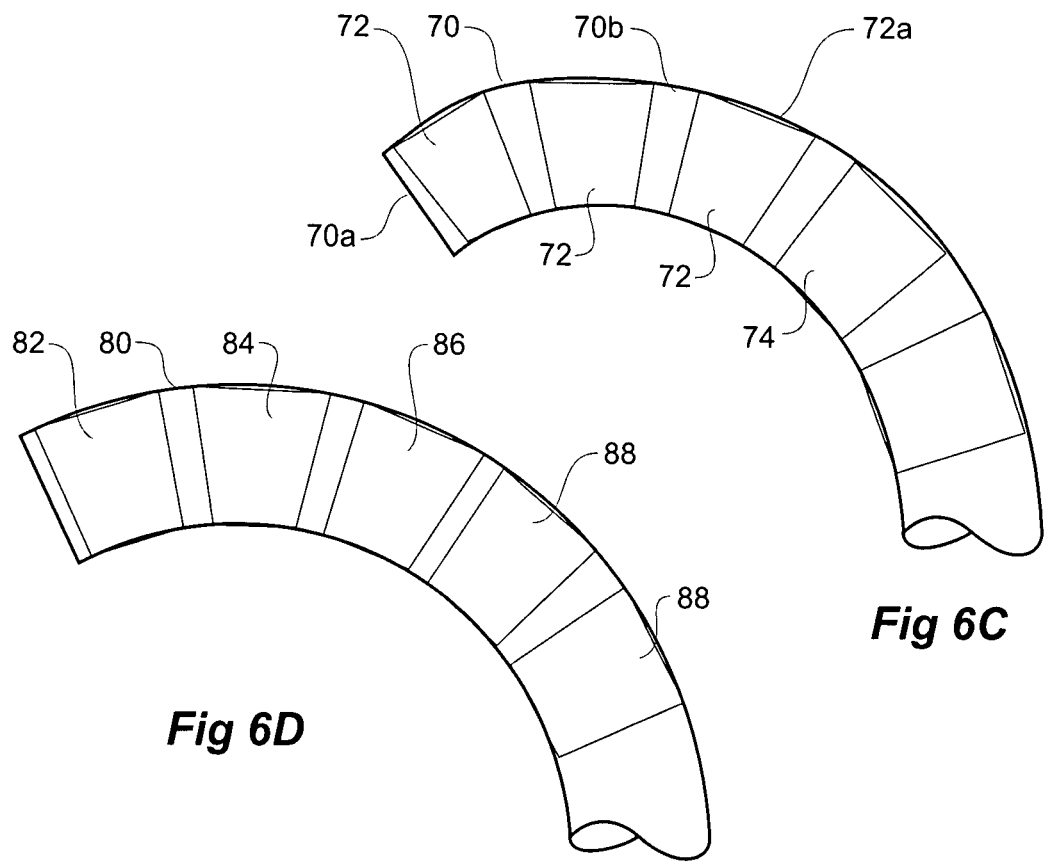
Fig 6C
Fig 6D

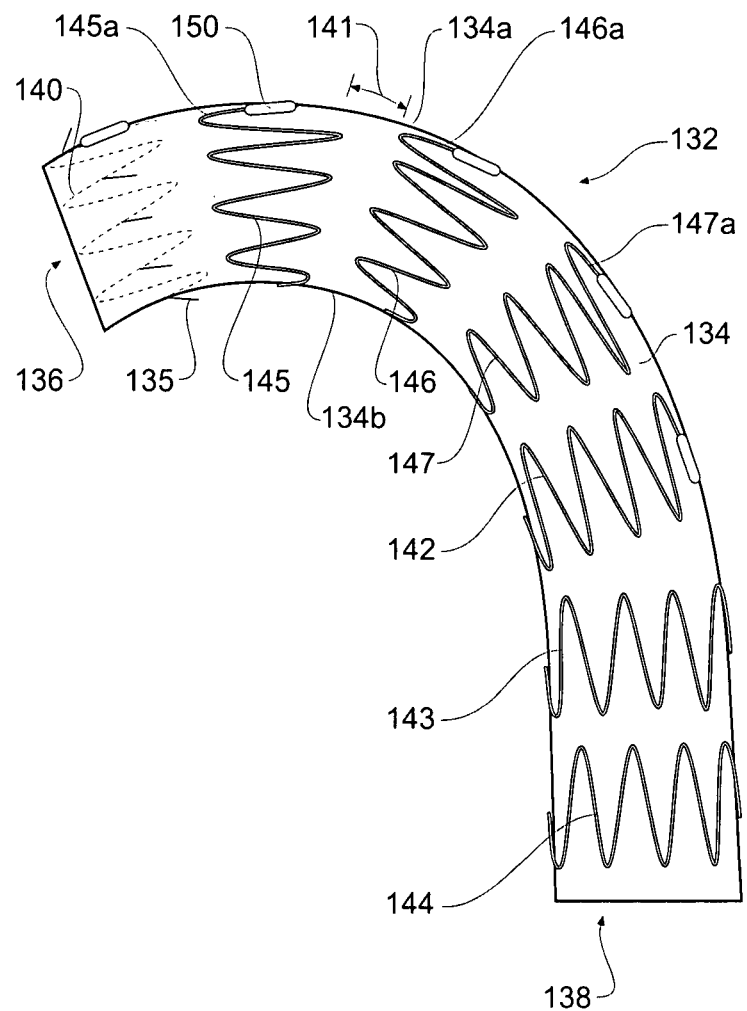
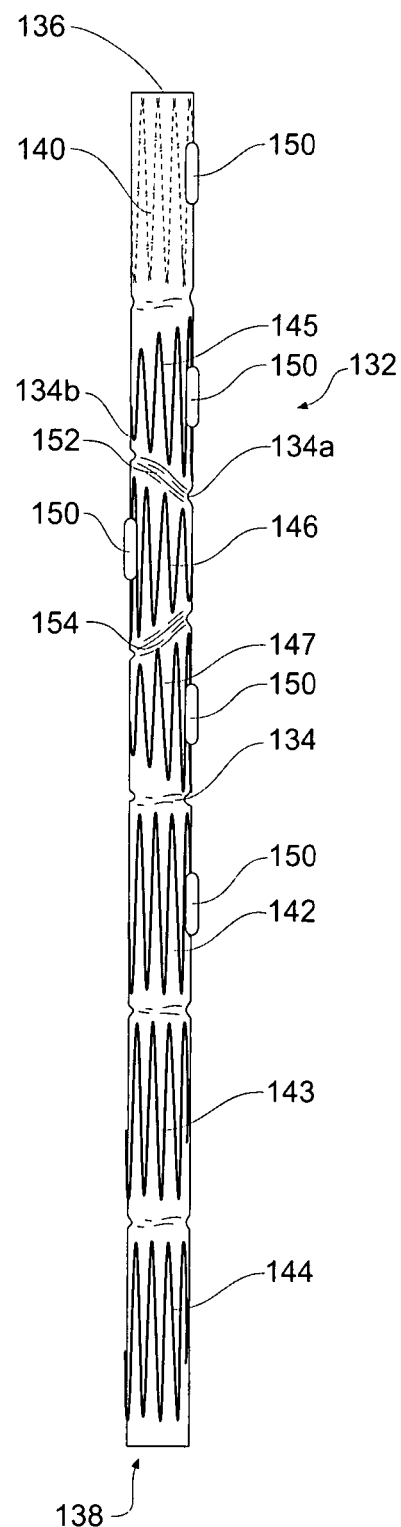
Fig 10
Fig 11

THORACIC ARCH STENT GRAFT AND METHOD OF DELIVERY

CROSS-REFERENCE TO RELATED APPLICATIONS

This application claims priority of provisional application Ser. No. 60/853,914, filed Oct. 24, 2006 and provisional application Ser. No. 60/853,915, filed Oct. 24, 2006.

TECHNICAL FIELD

This invention relates to a medical device and more particularly a stent and a stent graft incorporating the stent for deployment within the human or animal body and to a method by which such a stent graft can be deployed into the human or animal body.

BACKGROUND OF THE INVENTION

Stent grafts are used to replace or repair vessels of the body such as the blood vessels. A stent graft is usually formed from a tubular body of a biocompatible graft material and one or more stents are mounted into or onto the tubular body to provide support for the tubular body. The stents may be balloon expandable stents or self-expanding stents. This invention will be discussed with reference to the use of self-expanding stents but the invention is not limited to that and may be used with balloon expandable stents or other forms of stents.

Where a stent graft is to be placed into a curved blood vessel, and it is desired to maintain that curve, it is desirable to have the stent graft set into the approximate shape of the curve to prevent buckling of the stent graft in the vessel which may occlude some of the flow path in the vessel.

Stent grafts are deployed using endovascular techniques on an introduction device in which the stent graft is retained in a radially contracted condition by a sheath. Upon retraction of the sheath and release of any retention arrangement where necessary, where the stent graft has self expanding stents, the stent graft can expand under the action of the self expanding stents towards the vessel walls to define a blood flow path and the introduction device can be withdrawn.

There can be a problem with mounting of a stent graft designed for a curved vessel onto an essentially straight catheter of a deployment device. The catheter of a deployment device is essentially straight to enable it to be introduced through the vasculature of a patient via a femoral artery using the Seldinger technique.

It is an object of this invention to provide a stent, stent graft incorporating the stent which stent graft will form at least in part the shape of a curved vessel and to a method of deploying such a stent graft or to at least provide the physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

The term normal in relation to a stent is used to describe a stent which comprises a wire formed into a plurality of struts and bends between adjacent struts, the struts defining a cylindrical body and the bends at each end defining respective planes transverse to the longitudinal axis of the cylindrical body with the planes substantially parallel to each other and substantially at right angles to the longitudinal axis of the cylindrical body.

SUMMARY OF THE INVENTION

In one form therefore, the invention is said to reside in a stent comprising a wire formed into a plurality of struts and bends between adjacent struts, the struts defining a cylindrical body and the bends at each end defining respective planes transverse to the longitudinal axis of the cylindrical body wherein at least one of the planes is angled with respect to a plane at right angles to the longitudinal axis of the cylindrical body whereby the stent is tapered on one or both ends or is skewed. Preferably the stent is a zig zag stent comprising longer struts and shorter struts.

Preferably the wire is stainless steel or a shape memory whereby to form a self expanding stent.

In an alternative form the invention comprises a stent graft for curved lumens of the body, the stent graft comprising a tubular body of a graft material, at least a portion of which is arcuate to define an inner curved side and an outer curved side, the stent graft comprising a plurality of self expanding stents affixed thereto and spaced apart along at least a portion of the tubular body, there being a greater spacing apart between adjacent stents on the outer curved side than on the inner curved side on at least the arcuate portion of the tubular body.

Preferably the stents are zig-zag self expanding stents having a plurality of struts and bends between adjacent struts.

Preferably at least some of the stents are normal stents comprising a wire formed into a plurality of struts and bends between adjacent struts, the struts defining a cylindrical body and the bends at each end defining respective planes transverse to the longitudinal axis of the cylindrical body with the planes substantially parallel to each other and substantially at right angles to the longitudinal axis of the cylindrical body and at least some of the stents are tapered stents comprising a wire formed into a plurality of struts and bends between adjacent struts, the struts defining a cylindrical body and the bends at each end defining respective planes transverse to the longitudinal axis of the cylindrical body with at least one of the planes being angled with respect to the plane at right angles to the longitudinal axis of the cylindrical body whereby to define a tapered stent having one or two tapered ends.

Preferably at least some of the stents are tapered to define longer struts and shorter struts and the tapered stents are affixed to the tubular body with the longer struts on the outer curved side and the shorter struts on the inner curved side.

Preferably the tapered stents are mounted to the tubular body with the longer side on the outer curve of the tubular body.

Preferably the stent graft comprises first, second, third and subsequent stents from its proximal end, the first stent being a skewed stent, the second stent being a normal stent and the third stent being a skewed stent, the skew on the third stent being opposite to that of the first stent.

Alternatively the stent graft comprises first, second, third and subsequent stents from its proximal end, the first, second and third stents being tapered stents and wherein the tapered stents are mounted to the tubular body with their longer sides on the outer curve of the tubular body.

Alternatively the stent graft comprises first, second, third and subsequent stents from its proximal end, the first, second and third stents being tapered stents, the first stent comprising a taper on its distal end, the second stent comprising a taper at both its proximal and distal ends and the third stent comprising a taper on its proximal end and wherein the tapered stents are mounted to the tubular body with their longer sides on the outer curve of the tubular body.

Alternatively the stent graft comprises first, second, third and subsequent stents from its proximal end, the first stent being a tapered stent, the second stent being a normal stent and the third stent being a tapered stent and wherein the tapered stents are mounted to the tubular body with their longer sides on the outer curve of the tubular body.

Preferably the proximal-most stent is inside the tubular body and the remaining stents are on the outside of the tubular body.

In an alternative form the invention comprises a stent graft for curved lumens of the body, the stent graft having a tubular body of a graft material, at least a portion of which is arcuate to define an inner curved side and an outer curved side, the stent graft having a plurality of self expanding stents affixed thereto, at least some of the stents being tapered to define longer struts and shorter struts and the tapered stents being affixed to the tubular body with the longer struts on the outer curved side and the shorter struts on the inner curved side, the tapered stents being spaced apart longitudinally on the tubular body whereby the tubular body can be twisted substantially by half a turn between at least some of the adjacent stents when loaded into a deployment device whereby to nest the stents in the deployment device.

Preferably the tapered stents comprise a plurality of struts and bends between adjacent struts, the struts defining a cylindrical body and the bends at each end defining respective planes transverse to the longitudinal axis of the cylindrical body, and wherein at least one of the planes of the bends are at an angle transverse to the longitudinal axis of the cylindrical body, whereby to define a tapered stent comprising one or two tapered ends and wherein the tapered stent is mounted to the tubular body with the longer side on the outer curve of the tubular body.

Preferably the tapered stents are fastened to the tubular body at only their proximal or distal ends of the stent or intermediate their ends.

Preferably the circumferential twisting between adjacent tapered stents is each clockwise or anticlockwise twisting or alternatively clockwise and anticlockwise.

Preferably each of at least the tapered stents includes a radiopaque marker whereby the relative position of a stent being deployed with respect to a stent already deployed can be determined during deployment.

Preferably at least some of the stents have a marker on their longer sides whereby during deployment the introduction device can be rotated as each stent is released to ensure that each stent and hence the tubular body is correctly placed so that the arcuate portion is in a curved vessel in the desired orientation.

In an alternative form the invention comprises a stent graft introduction device in combination with a stent graft, the stent graft comprising a tubular body of a biocompatible graft material and comprising at least a portion nearer the proximal end thereof which is arcuate to define an inner curved side and an outer curved side, the stent graft having a plurality of stents affixed thereto, a first stent at the proximal end being a cylindrical normal self expanding stent, at least the next three stents being tapered stents and the balance of the stents to the distal end of the tubular body being cylindrical normal stents, the tapered stents being mounted to the tubular body such that their longer sides are on the outer curved side of the tubular body, at least the tapered stents having radiopaque markers thereon to facilitate alignment during deployment, the stent graft being retained on the introduction device such that there is a twist in one circumferential direction between the first tapered stent and a second tapered stent and a further twist in the same or the opposite circumferential direction between the second tapered stent and a third tapered stent whereby to nest adjacent stents with each other on the deployment device.

Although this invention is discussed in relation to deployment of a stent graft into the thoracic arch of a patient, the invention is not so limited and may be applied to other vessels of the human or animal body.

BRIEF DESCRIPTION OF THE DRAWING

This then generally describes the invention but to assist with understanding, reference will now be made to the accompanying drawings which show preferred embodiments of the invention.

In the drawings:

FIGS. 6A to 6D shows the embodiments of FIGS. 5A to 5D in a curved form;

FIG. 10 shows an alternative embodiment of a stent graft according to the present invention;

FIG. 11 shows the stent graft of FIG. 10 in a radially contracted and twisted condition for deployment;

DETAILED DESCRIPTION

Figure 1:
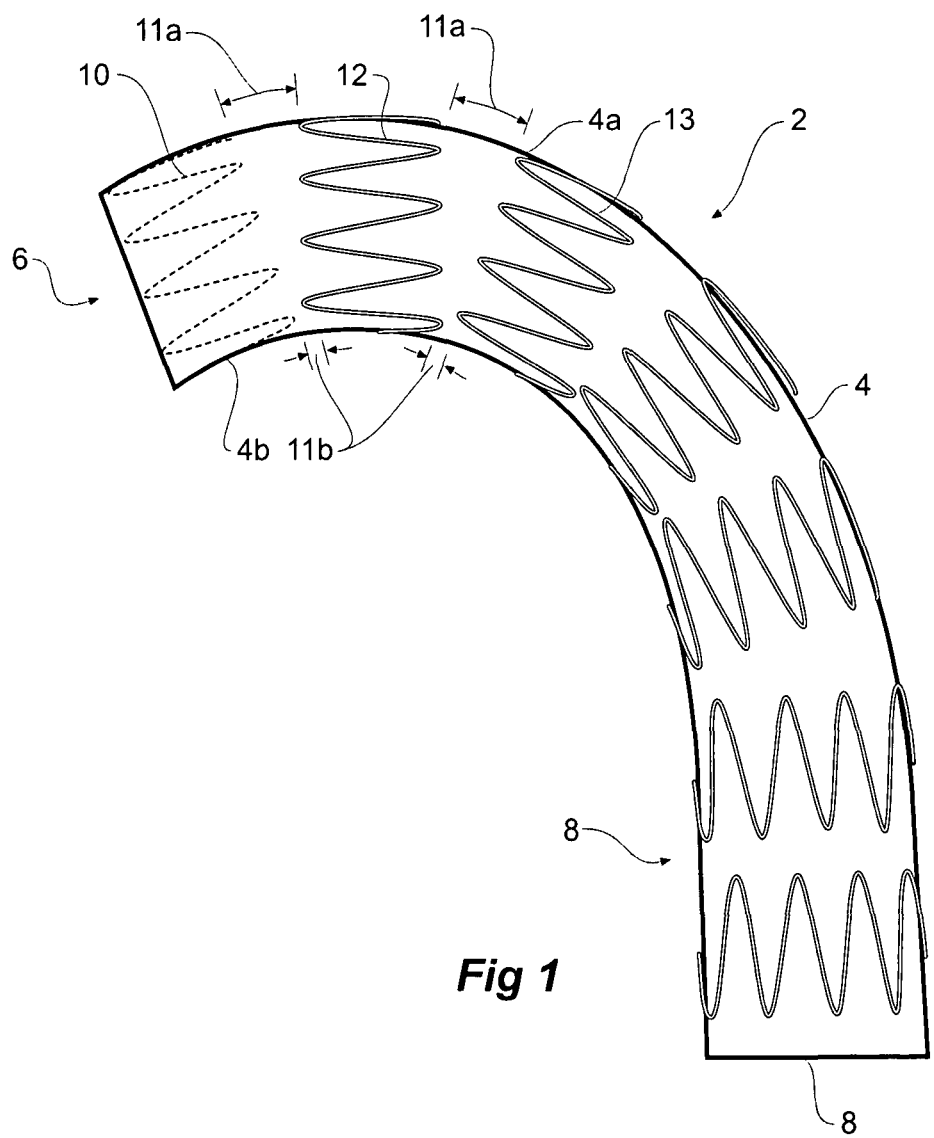
FIG. 1 shows a first embodiment of stent graft according to the present invention.
Figure 2:
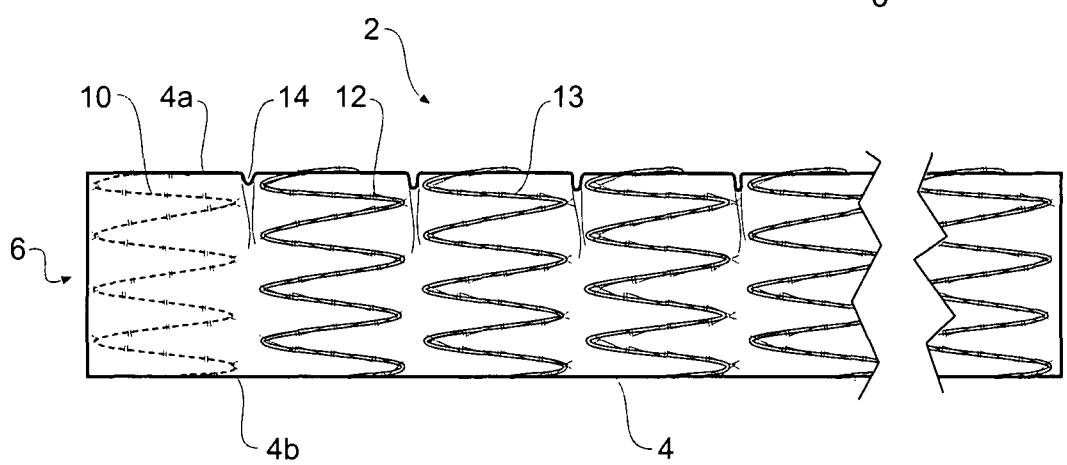
FIG. 2 shows the embodiment of a stent graft in FIG. 1 in straightened format.

Now looking at the drawings and in particular FIGS. 1 and 2, it will be seen that a first embodiment of stent graft 2 according to the present invention comprises a tubular body 4 of a biocompatible graft material with the tubular body formed into a curve at its proximal end 6 which approximates the curve of the thoracic arch of a aorta of a patient. The tubular body 4 formed into the arcuate curve has a outer curve 4a and an inner curve 4b. The distal end 8 is substantially straight to match the descending aorta of a patient. In this embodiment, the proximal-most stent 10 is inside the tubular body 4 and the remainder of these stents are on the outside of the tubular body.

In this embodiment, each of the stents 10, 12, 13 are of similar configuration and are not skewed or tapered.

The spacing of the stents 10 and 12, for instance, is greater, as shown by dimension 11a, on the outer curve 4a than on the inner curve 4b as is shown by the dimension 11b.

FIG. 2 shows the stent graft of FIG. 1 in a straightened format and to allow for the greater distance 11a (FIG. 1) between the first stent 10 and second stent 12 from the proximal end 6, the outer curve 4a is buckled at 14. At the inner curve 4b the graft material is not buckled between the stents.

Hence there is provided by this embodiment of the invention a stent graft which can be straightened for delivery by an introduction system and when released will take up a curved shape to conform to the curved shape of the vessel into which it is delivered.

Figure 3:
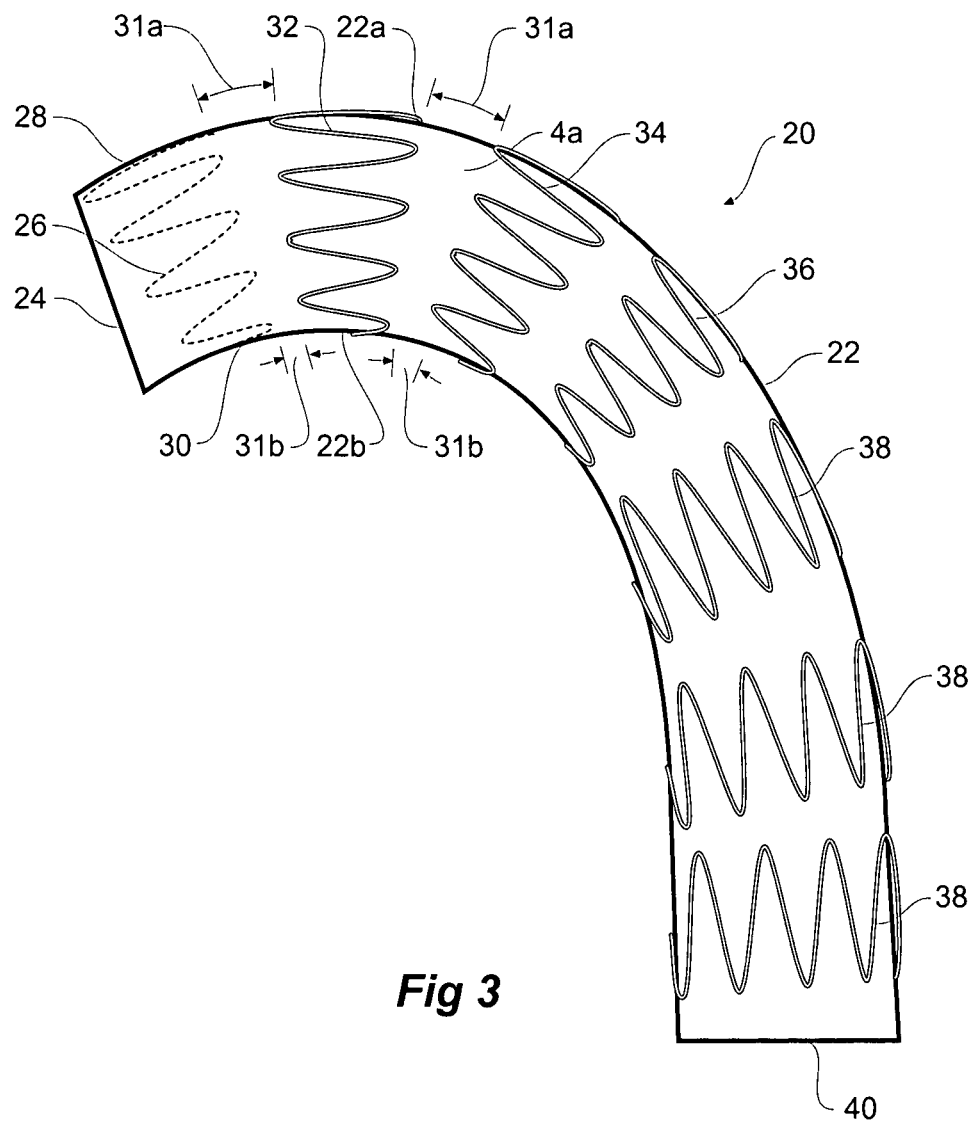
FIG. 3 shows an alternative embodiment of stent graft according to the present invention.
Figure 4:
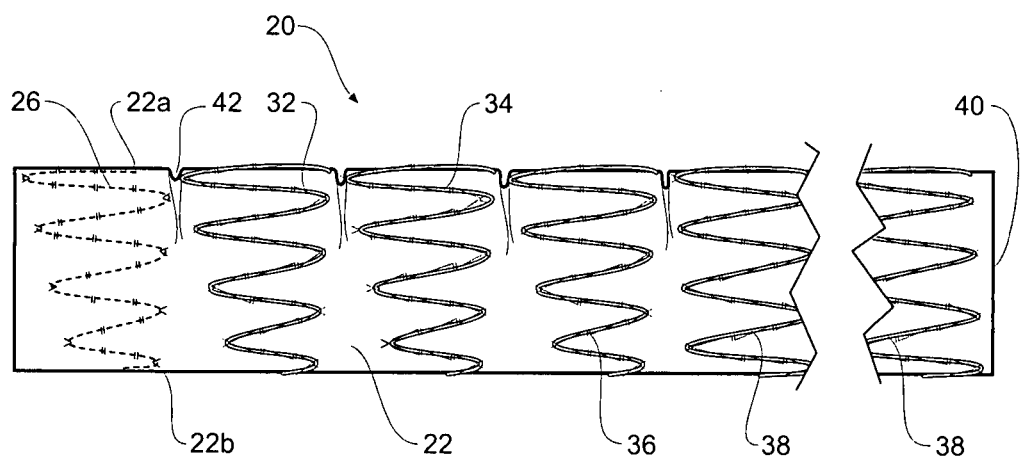
FIG. 4 shows the embodiment of stent graft in FIG. 3 in straightened format.

FIGS. 3 and 4 shows an alternative embodiment of stent graft according to this invention. In this embodiment again, the tubular body 22 of the stent graft 20 is curved at its proximal end 24 to define an outer curved side 22a and an inner curved side 22b. In this embodiment, the stents are tapered side to side and mounted onto the tubular body 22 such that the wider side 28 of the stent 26 is on the outer curve 22a and the narrower side 30 of the stent 26 is on the inner curve 22b. In this embodiment, there are four similarly tapered stents 26, 32, 34 and 36 from the proximal end 24 and three standard untapered stents 38 along the balance of the stent graft to the distal end 40. The stents 38 are on the substantially straight distal portion 40 of the stent graft 20.

The spacing of the stents 26 and 32, for instance, is greater, as shown by dimension 31a, on the outer curve 22a than on the inner curve 22b as is shown by the dimension 31b.

Again as shown in FIG. 4, when the stent is straightened out for loading into a deployment device, the outer side 22a of the tubular body 22 buckles at 42 but the inner side 22b is not buckled.

FIGS. 5A to 5D show various embodiments in a stylised form of stent graft according to the present invention and FIGS. 6A to 6D show the stylised stent grafts in their curved forms.

Figure 5A:
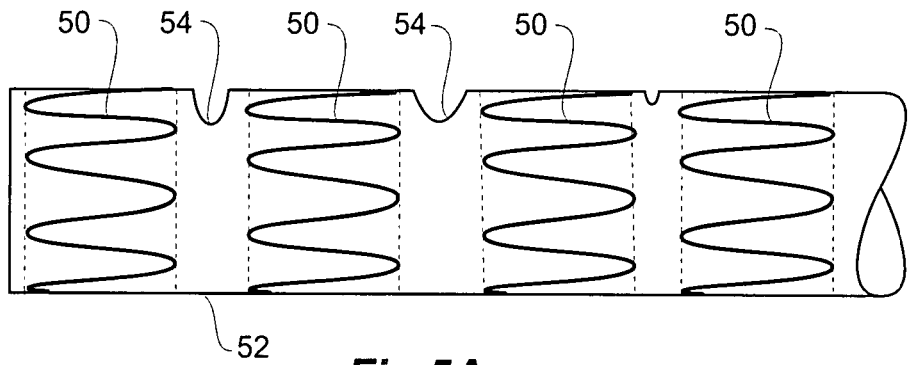
FIGS. 5A to 5D shows various embodiments of stent graft in stylised format.

FIG. 5A shows a stent graft with regular parallel sided stents 50 on a tubular body 52 but with buckled portions 54 between the first two stents on the outer curve side of the stent graft. Now looking at FIG. 6A, it will be noted that when the tubular body is put into its normal curved shape. It will be noted that the buckles disappear and the stent graft can take up its curved shape and that there is a greater distance between the stents on the outer side of the curve than on the inner side of the curve.

Figure 5B:
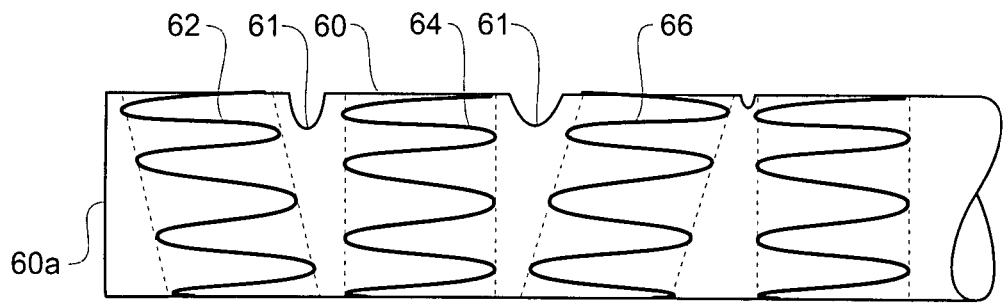

FIG. 5B shows a stent graft in which the tubular body 60 has a skewed stent 62, a straight-sided stent 64 and a further skewed stent 66 counting from the proximal end 60a. The tubular body has buckled portions 61 between each of the first three stents on the outer curve side of the stent graft. FIG. 6B shows the arrangement of the embodiment shown in FIG. 5B when in its curved form. It will be noted that the buckles disappear and the stent graft can take up its curved shape and that there is a greater distance between the stents on the outer side of the curve than on the inner side of the curve.

Figure 5C:
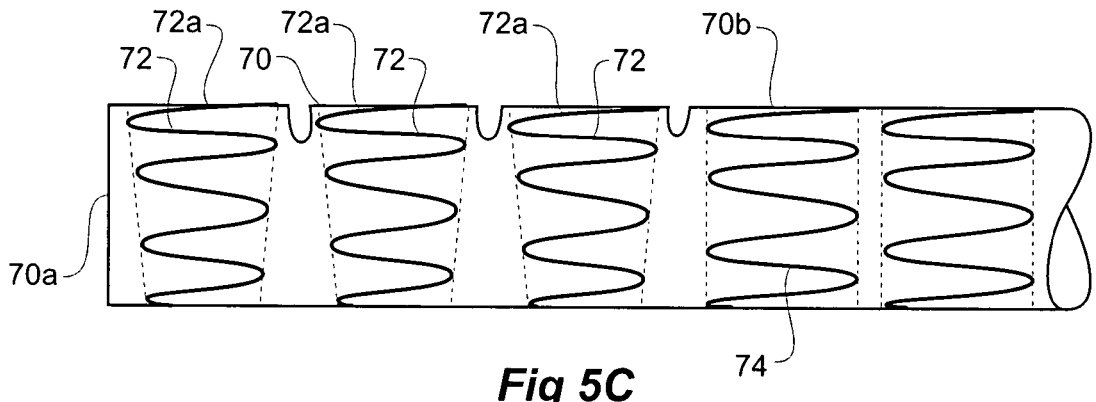

FIGS. 5C and 6c show an arrangement where a tighter curve is desirable. In this embodiment, the tubular body 70 has a greater curvature and the stents 72 at the proximal end 70a are each tapered with the wider side of the taper 72a on the outside of the curve 70b.

Figure 5D:
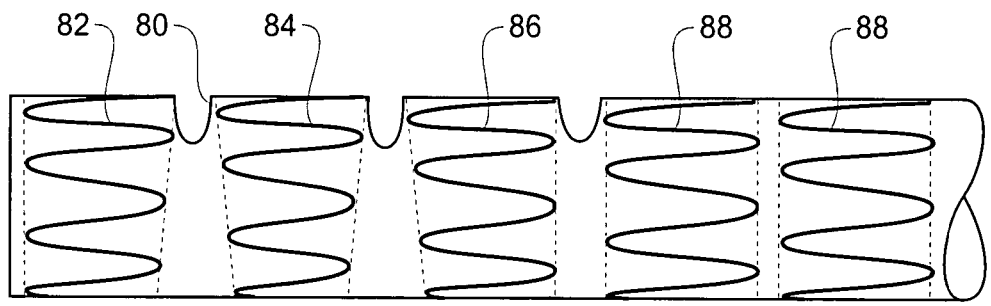

FIGS. 5D and 6D show a still further embodiment in which a tubular body 80 has a first stent graft 82 which is tapered on a distal side thereof, a second stent graft 84 which is tapered on both sides and a third stent graft 86 which is tapered on only a proximal side thereof, and then subsequent stents 88 are regular.

FIGS. 7A to 7D show various embodiments of zig-zag self-expanding stents according to the present invention.

Figure 7A:
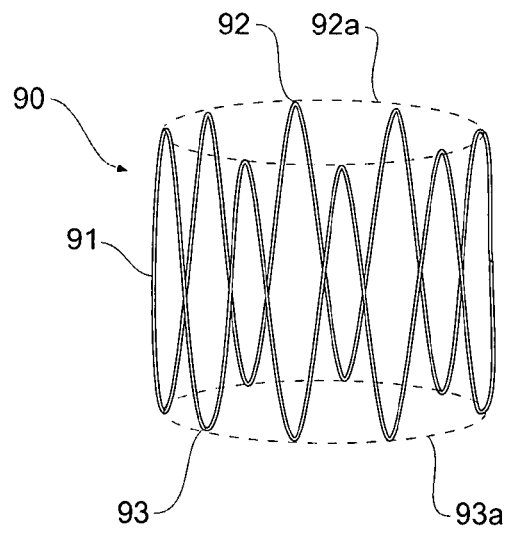
FIGS. 7A to 7D show various format of stent according to various embodiments according to the present invention.

FIG. 7A shows a standard or normal stent 90 formed from struts 91 and bends 92 at one end and 93 at the other end. The bends 92 at one end of the stent are in a first plane 92a which is substantially transverse to the longitudinal axis of the stent and the bends 93 at the other end of the stent are in a second plane 93a which is parallel to the first plane 92a and substantially transverse to the longitudinal axis of the stent.

Figure 7B:
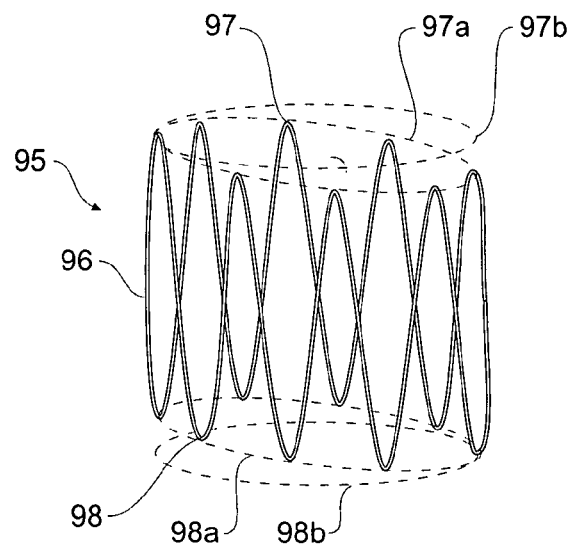

FIG. 7B shows a skewed stent 95 which is in the form of a series of struts 96 and bends 97 at one end and 98 at the other end. The bends 97 form a plane 97a which is at an angle to the longitudinal axis of the stent graft and the bends 98 lie in a plane 98a which is at an angle to the longitudinal axis and substantially parallel to the plane 97a of the bends 97. Both the planes 97a and 98a are at an angle to normal planes 97b and 98b respectively at each end of the stent graft and are substantially parallel to each other.

Figure 7C:
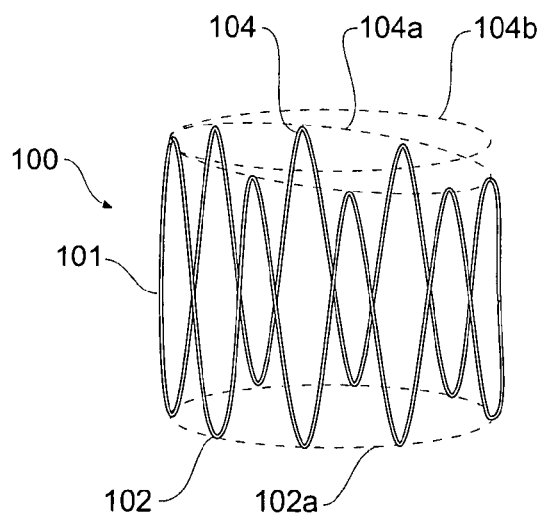

Stent 100 in FIG. 7C is a half tapered stent with the bends 102 at one end being in a plane 102a which is substantially transverse or normal to the longitudinal axis of the stent graft but the bends 104 being in a plane 104a which is at an angle to the longitudinal axis of the stent graft. The plane 104a is at an angle to normal plane 104b and 102a respectively at each end of the stent graft.

Figure 7D:
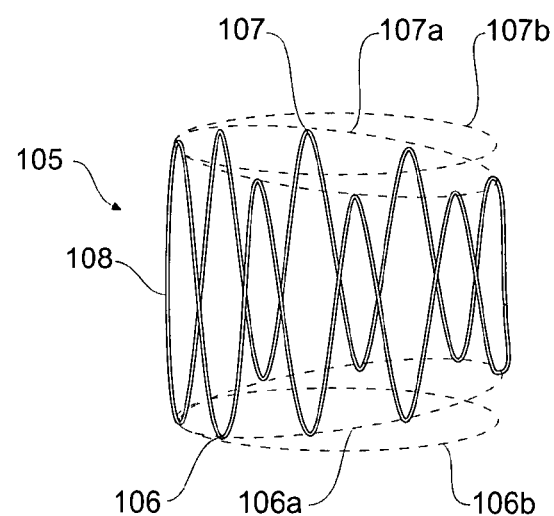

FIG. 7D shows a stent 105 which is tapered on both ends such that the bends 106 form a first plane 106a which is at an angle and the bends 107 form a plane 107a which is at another angle. Both the planes 106a and 107a are at an angle to normal planes 106b and 107b respectively at each end of the stent graft.

The wire which forms the stents can be stainless steel or Nitinol™ or any other suitable material.

Figure 8:
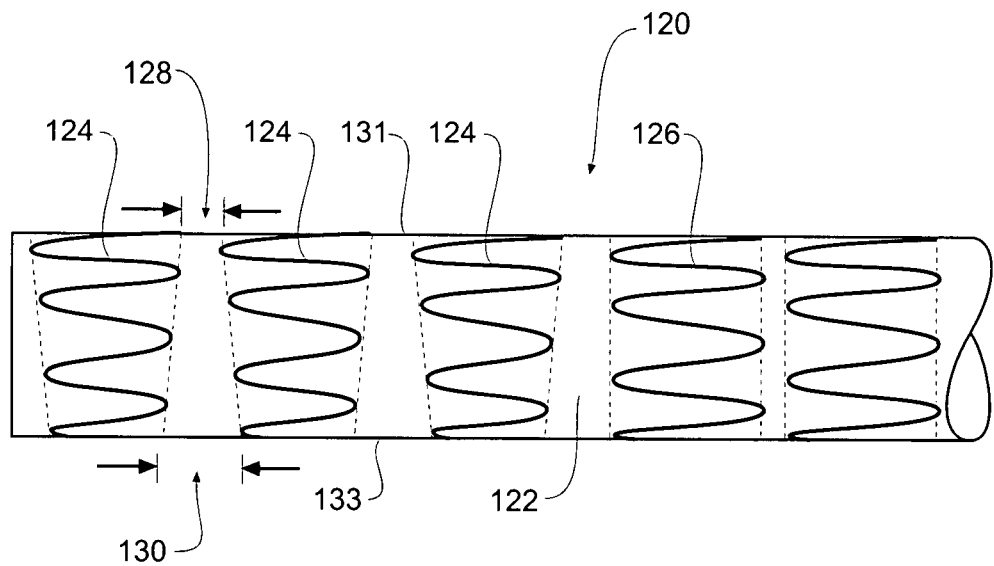
FIG. 8 shows a portion of a further embodiment of stent graft according to the present invention.
Figure 9:
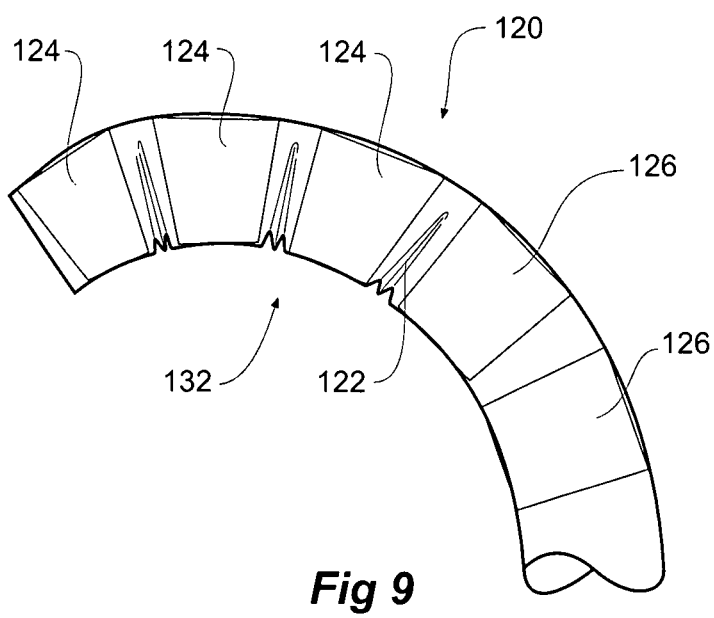
FIG. 9 shows the embodiment of FIG. 8 when the stent graft is in a curved configuration.

FIGS. 8 and 9 show an alternative embodiment of a stent graft incorporating stents according to the present invention. In this embodiment the stent graft 120 has a tubular body 122 which at rest is substantially straight. The tubular body is supported by a plurality of stents comprising tapered stents 124 and straight or normal stents 126. The stents are fastened to the tubular body by stitching or other suitable means. The stents 124 and 126 can be on the inside or the outside of the tubular body 122. The tapered stent are fastened to the tubular body so that their longest struts are on the same side 131 of the tubular body at a common circumferential position on the tubular body. Between the tapered stents 124 on that side 131 of the tubular body the spacing of stents 128 is less than the spacing 130 on a diametrically opposed side 133. This means that when the stent graft is bent with the wider portions of the stent on the outside of a curve such as in a curved vessel of the human or animal body the material of the other side 133 with the wider spacing 130 can buckle more to enable the stent graft to take up the curved shape.

When the stent graft 120 is deployed within a curved vessel of the human or animal body with the longer struts of the stent on the outside of the curve the stent graft can take up the configuration shown in FIG. 9. It will be noted that the material of the stent graft buckles between the stents on the inside of the curve 132.

FIG. 10 shows an alternative embodiment of a stent graft according to the present invention The stent graft 132 according to the present invention comprises a tubular body 134 of a biocompatible graft material with the tubular body formed into a curve adjacent its proximal end 136 which approximates the curve of the thoracic arch of an aorta of a patient. The tubular body 134 is formed into the arcuate curve to define a outer curve 134a and an inner curve 134b. The tubular body towards the distal end 138 is substantially straight to match the descending aorta of a patient. In this embodiment, the proximal-most stent 140 is inside the tubular body 134 and the remainder of these stents are on the outside of the tubular body.

In this embodiment, each of the stents 140, 142, 143 and 144 are of similar cylindrical configuration and are not tapered being of the type shown in FIG. 7A. The stents 145, 146 and 147 are tapered with their longer sides 145a, 146a and 147a on the outer side 134a of the curved tubular body 134 and are of the type shown in FIG. 7D. The stents are affixed to the tubular body by stitching or other suitable means (not shown). The spacing of the stents 145 and 146 is as shown by dimension 141 on the outer curve 134a is sufficient to enable the tubular body 134 to be circumferentially twisted through substantially half a turn between the stent 145 and the stent 146. Similarly the spacing of the stents 146 and 147 is sufficient to enable the tubular body 134 to be circumferentially twisted through substantially half a turn between the stent 146 and the stent 147.

The proximal cylindrical stent 140 has a plurality of distally facing barbs 135 which when the stent graft is deployed and released with the thoracic arch engage with the wall of the aorta and prevent distal migration of the stent graft.

Each of the stents 140, 145, 146, 147 and 142 has a radiopaque marker 150. On the cylindrical stents 140 and 142 the radiopaque marker 150 is positioned so that it is on the outer curve of the stent graft when mounted onto the stent graft. On the tapered stents 145, 146 and 147 the radiopaque marker 150 is positioned on the longest strut of each stent so that again it is on the outer curve of the stent graft when mounted onto the stent graft. For the purpose of assisting alignment of the radiopaque markers on the stents onto the tubular graft material on the outer curve there may be provided on the graft material a longitudinal line (not shown) aligned with the outer curve.

Alternatively the radiopaque markers can be placed on the shortest strut and the line on the tubular graft material on the inner curve there may be provided on the graft material a longitudinal line (not shown) aligned with the inner curve.

FIG. 11 shows the stent graft of FIG. 10 in a straightened and twisted form as it would be mounted onto a deployment device according to the present invention. In this state there would normally be a sheath holding the stent graft in the compressed condition but the sheath has been omitted so that the stent graft can be seen. The tubular body 134 of the stent graft 132 and each of the stents 140, 145, 146, 147, 142, 143 and 144 are radially compressed. Between the stent 145 and the stent 146 the tubular body 134 is twisted circumferentially through approximately half a turn 152 so that the radiopaque marker 150 on stent 146 is on the other side of the tubular body. Between the stent 146 and the stent 147 the tubular body 134 is twisted circumferentially through approximately half a turn 154 so that the radiopaque marker 150 on stent 147 is on the original side of the tubular body. The half a turn 154 is in the opposite direction than the half a turn 152 so that during deployment the tubular body distal of the stent 147 does not need to be rotated.

It will be noted that the stent 146 is nested between the stents 145 and 147 because of the taper angles coinciding after the stent 146 has been rotated as discussed above.

Hence there is provided by this embodiment of the invention shown in FIGS. 10 and 11 a stent graft which can be straightened for mounting onto and delivery by an introduction system and when released will take up a curved shape to conform to the curved shape of the vessel into which it is delivered.

FIGS. 12 to 17 show a schematic view of the thoracic arch and descending aorta of a patient with a deployment device including a stent graft according to the present invention deployed into the thoracic arch and the sequential stages of deployment of the stent graft of the type shown in FIGS. 10 and 11.

Figure 12:
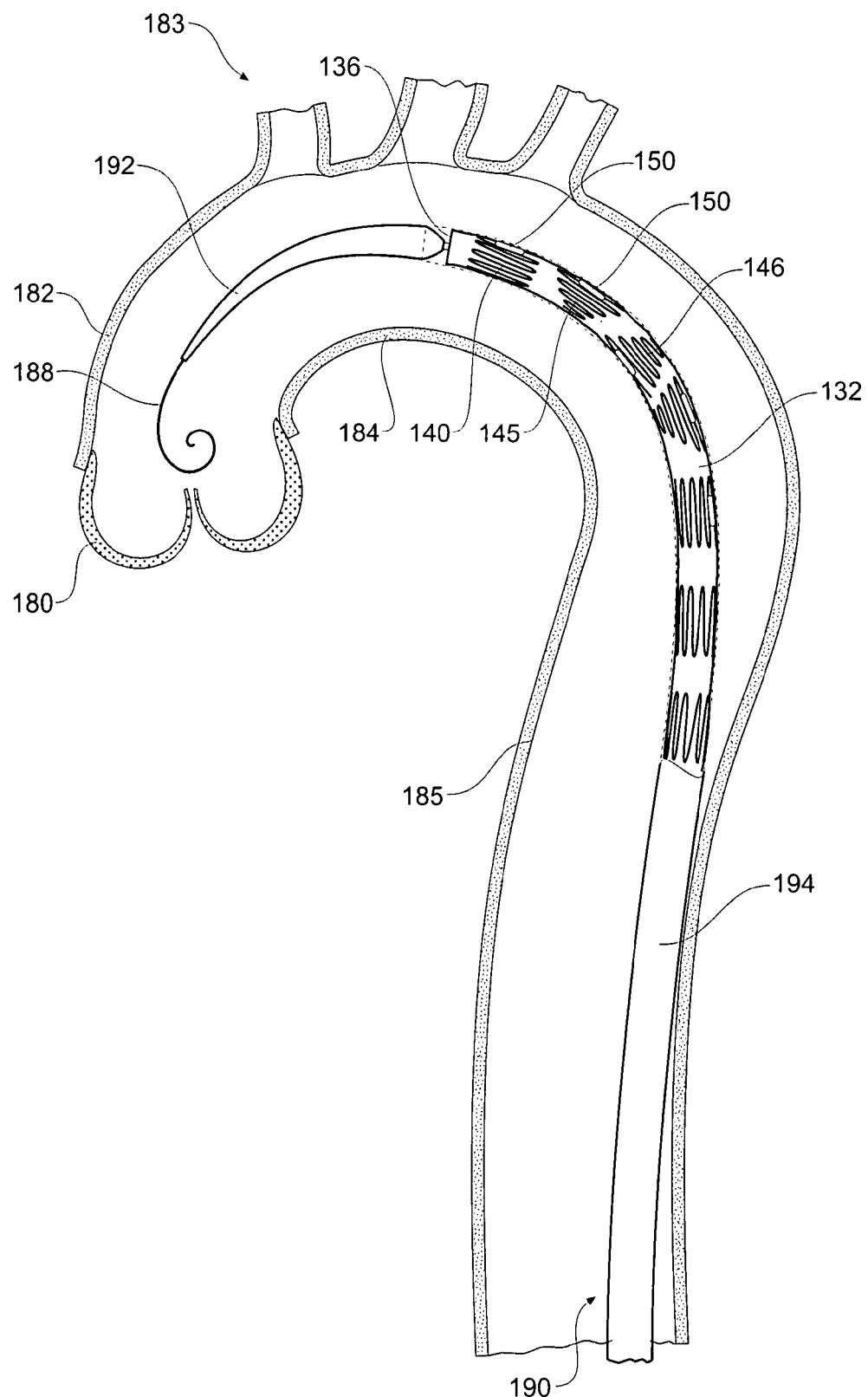
FIG. 12 shows a schematic view of the thoracic arch and descending aorta of a patient with a deployment device including a stent graft according to the embodiment of FIG. 10 of the present invention deployed into the thoracic arch.

FIG. 12 shows a schematic view of the aorta of a patient. The aorta commences at the aortic valve 180 of the heart and an ascending aorta 182 extends to the arch vessels 183 at the thoracic arch 184 and then the descending aorta 185 extends down the truck of the body of the patient. A guide wire 188 has been introduced to extend over thoracic arch towards aortic valve 180 and over that guide wire has been advanced a deployment device 190. The deployment device 190 includes a nose cone dilator 192 and a sheath 194 extending up to the nose cone dilator. The sheath 194 is shown transparent so that the stent graft 132 and stents 140, 145 and 146 restrained in a contracted condition within the introduction device and the radiopaque markers 150 can be seen.

The introducer 190 is advanced to the desired placement site for the stent graft and rotated so that the opaque marker 150 on the first stent 140 and second stent 145 from the proximal end 136 are on the outer side of the curve as can be seen by the position of the radiopaque markers 150.

Figure 13:
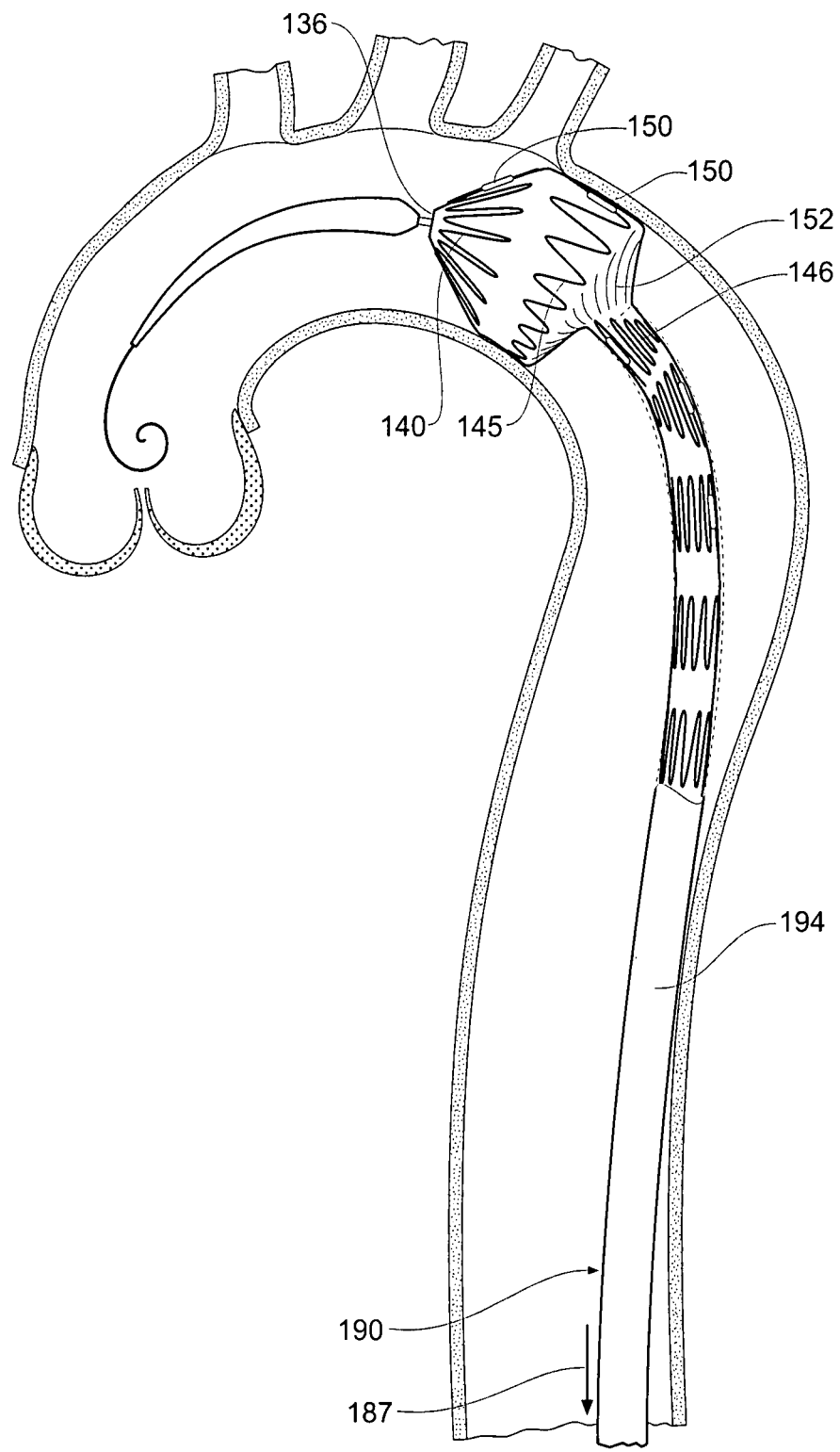
FIGS. 13 to 17 show sequential stages of deployment of the stent graft shown in FIG. 11.

The next stage is shown in FIG. 13.

In FIG. 13 the sheath 194 of the introduction device 190 has been retracted as shown by the arrow 187 so that the first stent 140 and second stent 145 are released from the sheath. At this stage the proximal end 136 of the stent graft is still retained onto the delivery device by a retention and release means (not shown). It will be noted, too, that the twist 152 in the graft material between the stent 145 and stent 146 can be seen.

Figure 14:
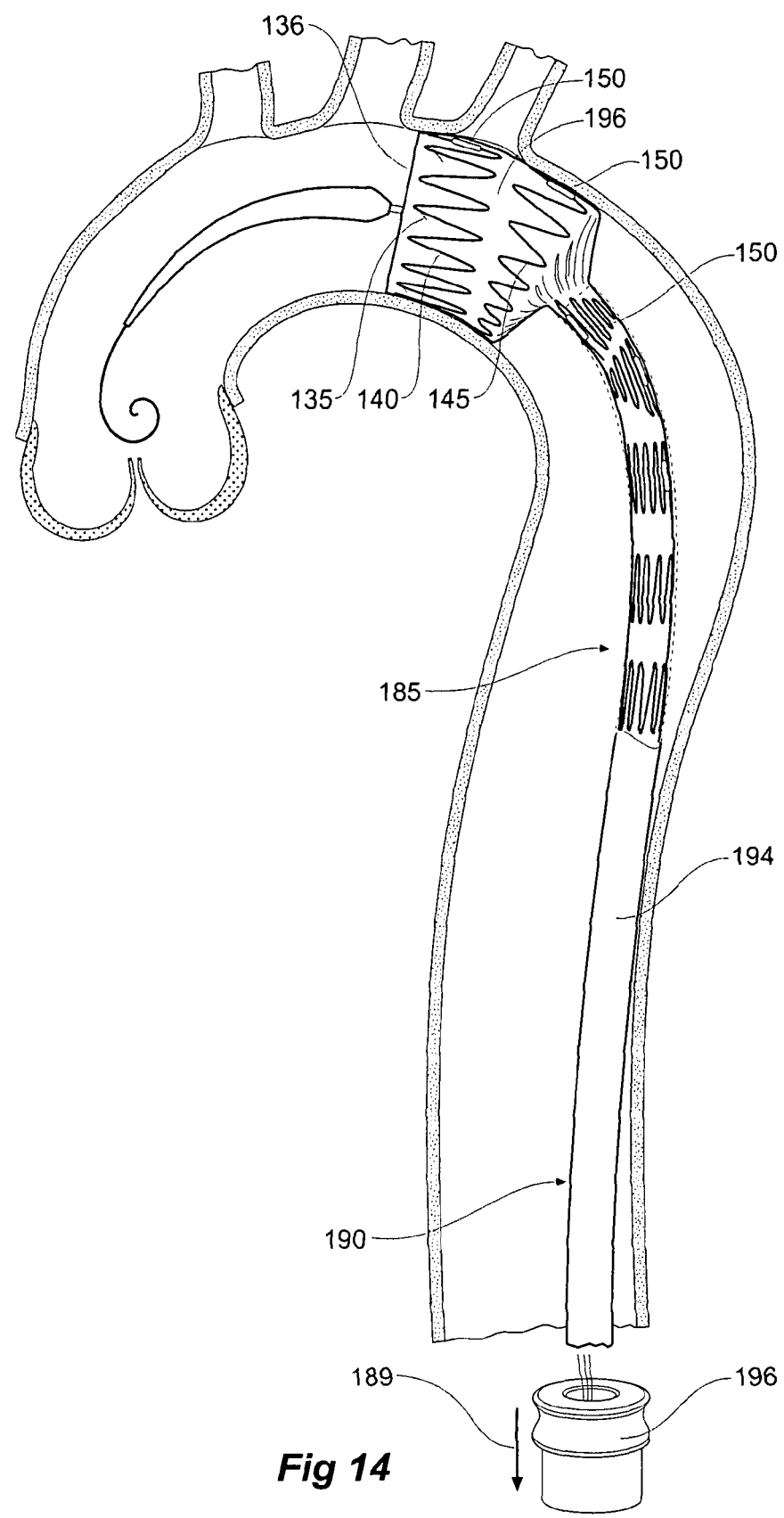

In the next stage as shown in FIG. 14 a release arrangement 196 (which is mounted on a release handle (not shown) for the delivery device 190) for the proximal end 136 of the stent graft 196 is actuated as shown by the arrow 189 so that the proximal end 136 expands to the diameter of the aorta and the barbs 135 engage into the wall of the aorta.

Figure 15:
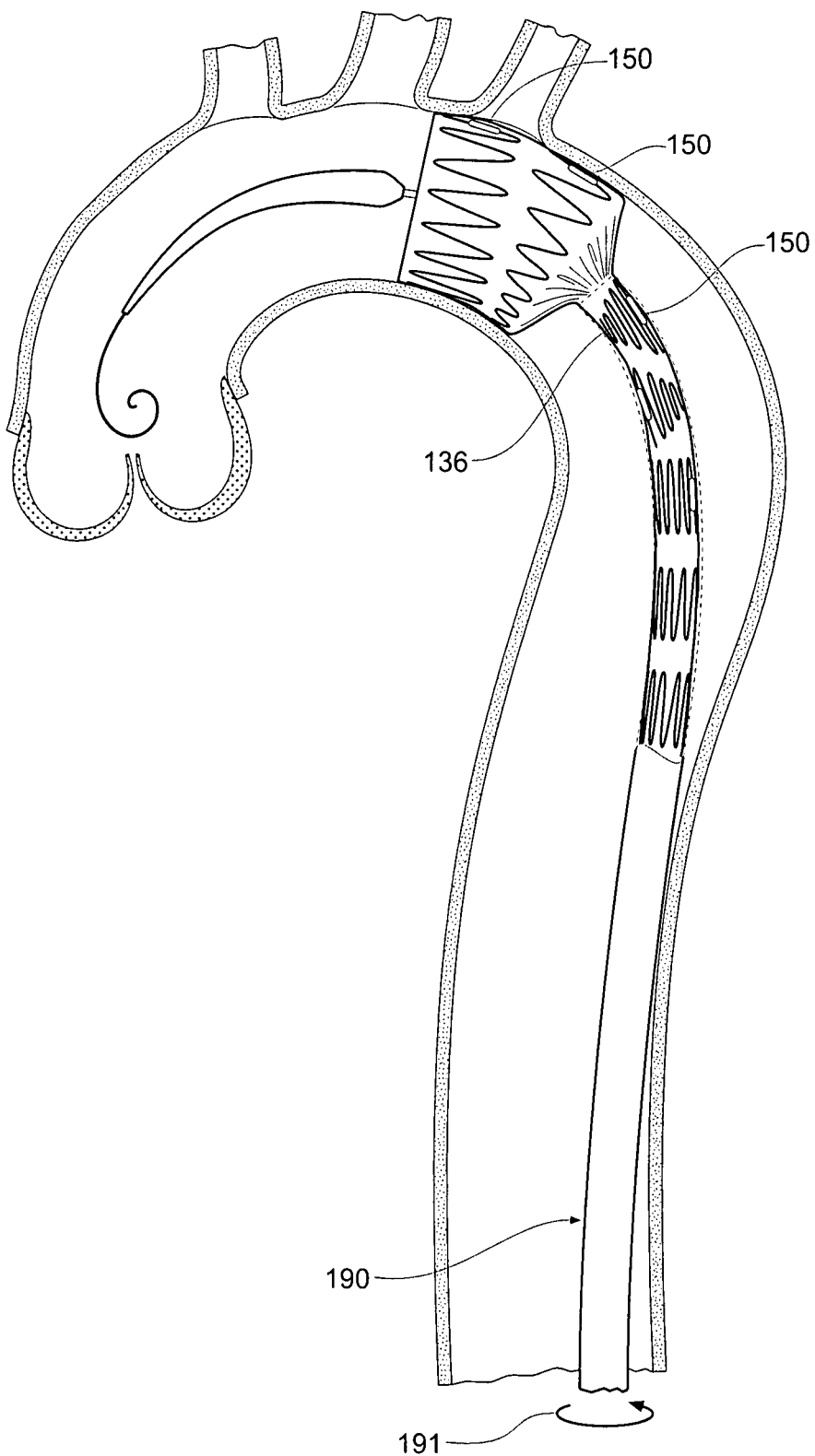

In the next stage as shown in FIG. 15 the delivery device 190 is rotated in a clockwise direction as shown by the arrow 191 to release the twist 152 and to bring the marker 150 on the stent 146 to the outside of the curve. At this stage, however, the stent 146 is still retained within the sheath 194.

Figure 16:
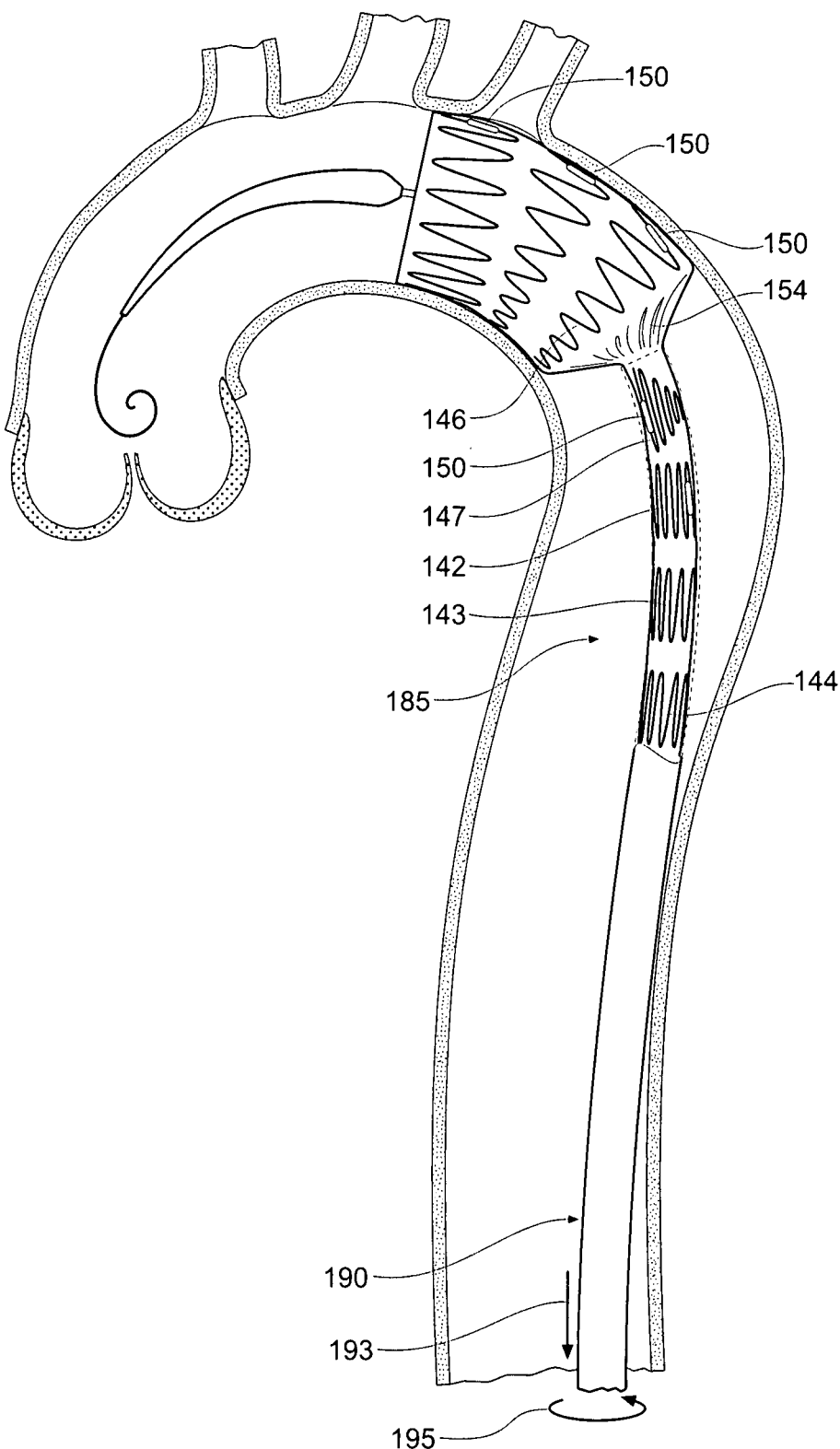

In the next stage as shown in FIG. 16 the sheath 194 of the delivery device 190 is then retracted as shown by the arrow 193 to release the stent 146 so that it can expand to the diameter of the vessel. At this stage the twist 154 between the stent 146 and stent 147 is partially exposed. At this stage, however, the stent 147 is still retained within the sheath 194.

Figure 17:
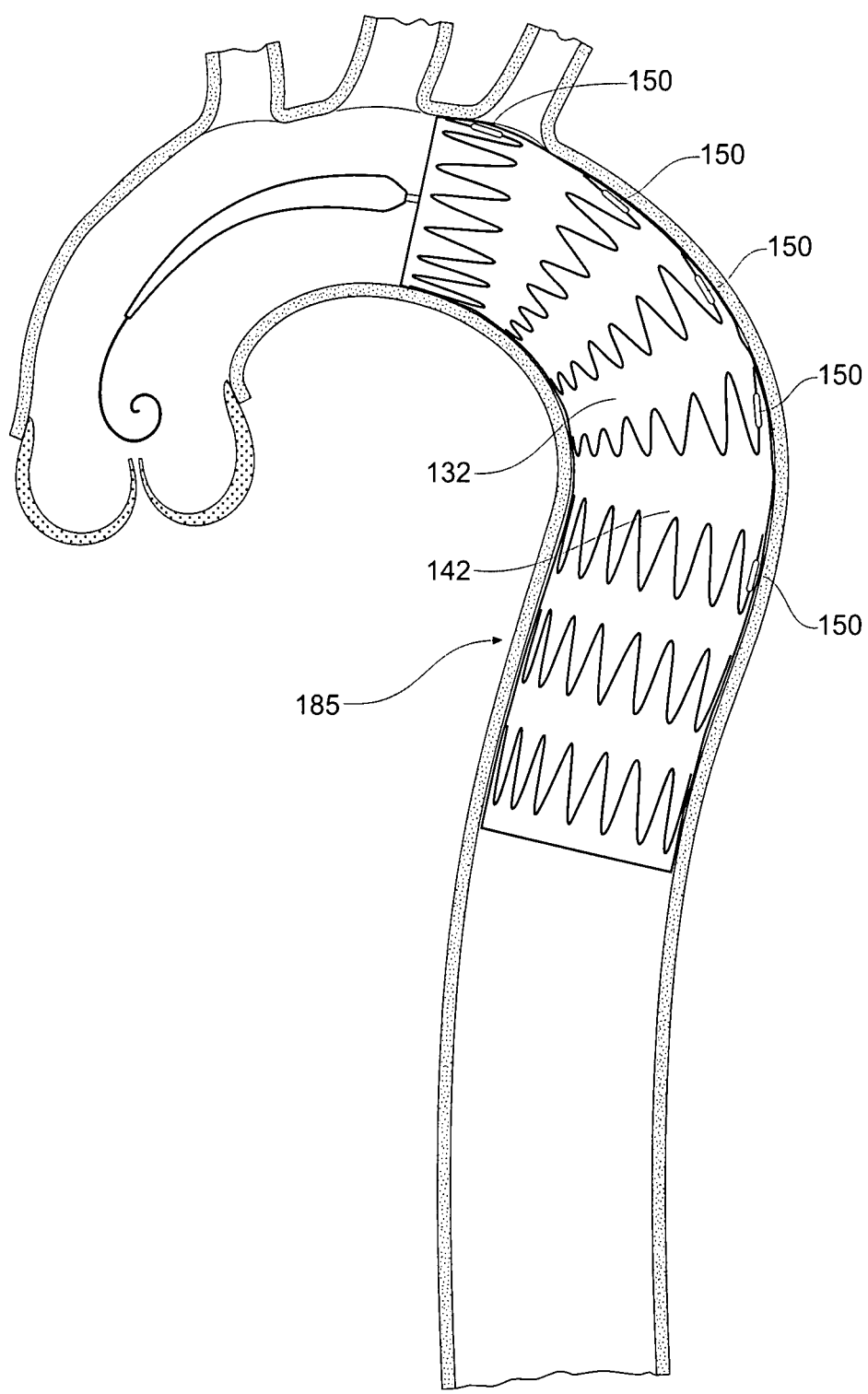

The sheath 194 can again be rotated as shown by the arrow 195 to release the twist 154 and bring the marker 150 on the stent 147 to the outside of the curve. The sheath 194 of the deployment device 190 is then retracted so that the stents 17 and 12, 13 and 14 are exposed as shown in FIG. 17. The entire delivery device can then be removed leaving the stent graft in position in the thoracic arch and descending aorta.

In an alternative arrangement where the twists 152 and 154 are formed in opposite circumferential directions an alternative release arrangement can be used. After the stage shown in FIG. 14 when the proximal end of the stent graft has been released to engage the walls of the vessel retraction of the sheath 194 with continued tension on the material of the stent graft will cause the stent 146 to rotate automatically to its desired position with its longer struts on the outside of the curve. This means that there does not have to be any rotation of the delivery device between the release of the stents. This may be advantageous where the vasculature is very distorted.

Figure 18A:
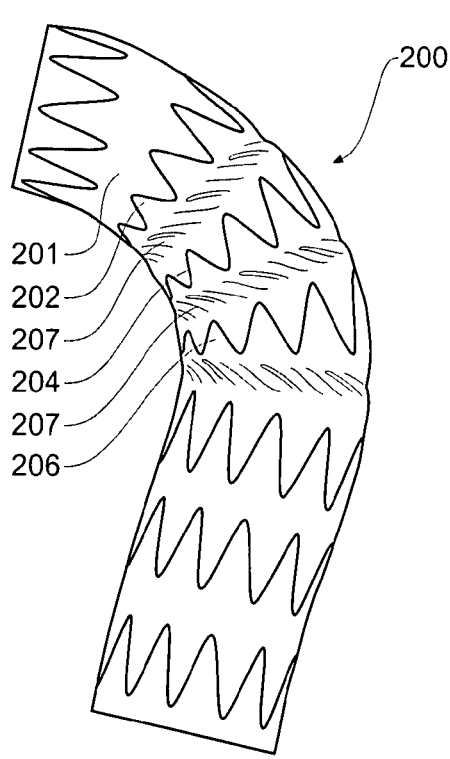
FIG. 18A shows an embodiment of a stent graft according to the present invention.

FIG. 18A shows an alternative embodiment of stent graft according to the present invention. In this embodiment the stent graft 200 has the tapered stents 202, 204 and 206 sewn onto the curved tubular body 201 with a slight twist 207 engineered into the stent graft material to compensate for the opposite twist needed for nesting the stents in the delivery system when it is mounted into the delivery system.

Figure 18B:
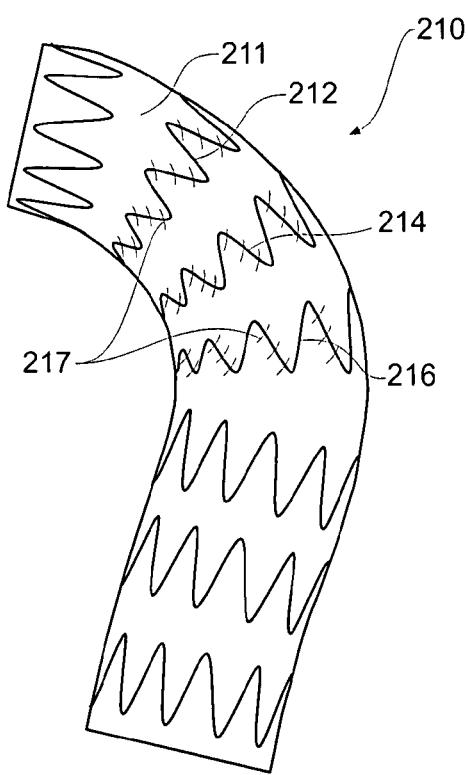
FIG. 18B shows a further embodiment of a stent graft according to the present invention specifically showing an alternative mounting of stents onto the graft material.

FIG. 18B shows an alternative embodiment of stent graft according to the present invention. In this embodiment the stent graft 210 the tapered stents 212, 214 and 216 sewn onto the curved tubular body 211 with directional sewing 217 to allow the twisting needed for nesting stents in the delivery system to extend under the stents 212, 214 and 216.

Figure 18C:
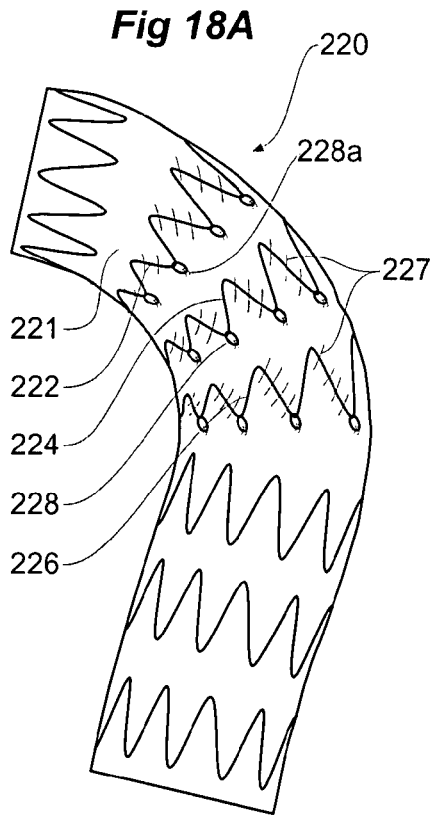
FIG. 18C shows another embodiment of a stent graft according to the present invention specifically showing an alternative mounting of stents onto the graft material.

FIG. 18C shows an alternative embodiment of stent graft according to the present invention. In this embodiment the stent graft 220 tapered stents 222, 224 and 226 are sewn into the curved tubular body 221 with a combination of directional sewing stitches 227 and stitches 228a through eyelet 228 at the bends at a first end of each stent. The stitching through each eyelet keeps the first end of each stent in its selected place on the tubular body but enables movement of graft material under each stent at the other end of each stent.

Figure 18D:
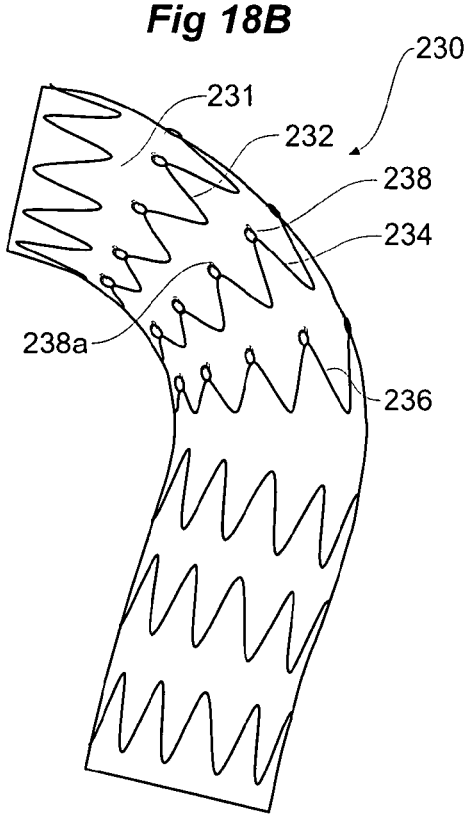
FIG. 18D shows an embodiment of a stent graft according to the present invention specifically showing an alternative mounting of stents onto the graft material.

FIG. 18D shows a still further embodiment of stent graft 230 according to the present invention. In this embodiment the tapered stents 232, 234 and 236 are sewn into the curved tubular body 231 with stitches 238a through eyelets 238 at the bends at a first end of each stent. The stitching through each eyelet keeps the first end of each stent in its selected place on the tubular body but enables movement of graft material under each stent at the second end of each stent.

It will be seen that by this invention a stent graft assembly can be formed which will more easily take up the form of a curved portion of a vasculature of a patient.

Throughout this specification various forms of the invention are discussed but the invention not is limited to any one of these but may reside on two or more combined together. The examples are given for illustration only and not for limitation.

What is claimed is:

1. A stent graft introduction device in combination with a stent graft, the stent graft comprising a tubular body of a biocompatible graft material, at least a portion of which tubular body is arcuate to define an inner curved side of the tubular body and an outer curved side of the tubular body, the stent graft comprising a plurality of self expanding stents affixed thereto and spaced apart along at least a portion of the tubular body, wherein at least some of the stents are normal stents comprising a wire formed into a plurality of struts and bends between adjacent struts, the struts defining a cylindrical body and the bends at each end defining respective planes transverse to the longitudinal axis of the cylindrical body with the planes substantially parallel to each other and substantially at right angles to the longitudinal axis of the cylindrical body and at least some of the stents are tapered stents comprising a wire formed into a plurality of struts and bends between adjacent struts, the struts defining a cylindrical body and the bends at each end defining respective planes transverse to the longitudinal axis of the cylindrical body with at least one of the planes being angled with respect to the plane at right angles to the longitudinal axis of the cylindrical body whereby to define a tapered stent having one or two tapered ends and wherein the tapered stents are affixed to the tubular body with the longer struts on the outer curved side of the tubular body and the shorter struts on the inner curved side of the tubular body a proximal stent at the proximal end of the tubular body being a normal self expanding stent, at least the next three stents being tapered stents and the balance of the stents at a distal end of the tubular body being normal stents, the next three stents being a first tapered stent, a second tapered stent and a third tapered stent, the first, second and third tapered stents being mounted to the tubular body such that their longer sides are on the outer curved side of the tubular body, at least the tapered stents having radiopaque markers thereon to facilitate alignment during deployment, the stent graft being retained on the introduction device such that there is a twist in one circumferential direction between the first tapered stent and a second tapered stent and a further twist in the same or the opposite circumferential direction between the second tapered stent and a third tapered stent whereby to nest adjacent stents with each other on the deployment device.

2. A stent graft introduction device in combination with a stent graft as in claim 1 wherein the first tapered stent comprises a taper on its distal end, the second tapered stent comprises a taper at both its proximal and distal ends and the third tapered stent comprises a taper on its proximal end.

3. A stent graft introduction device in combination with a stent graft as in claim 1 wherein a proximal stent is inside the tubular body and the remaining stents are on the outside of the tubular body.

4. A stent graft introduction device in combination with a stent graft as in claim 1 wherein the tapered stents are spaced apart longitudinally on the tubular body whereby to assist the tubular body being twisted.

5. A stent graft introduction device in combination with a stent graft as in claim 4 wherein the circumferential twisting between adjacent tapered stents is each clockwise or anti-clockwise twisting or alternatively clockwise and anticlockwise.

6. A stent graft introduction device in combination with a stent graft as in claim 4 wherein each of at least the tapered stents includes a radiopaque marker whereby the relative position of a stent being deployed with respect to a stent already deployed can be determined during deployment.

7. A stent graft introduction device in combination with a stent graft as in claim 4 wherein the stents have a radiopaque marker on their longer sides whereby during deployment the introduction device can be rotated as each stent is released to ensure that each stent and hence the tubular body is correctly placed so that the arcuate portion is in a curved vessel in the desired orientation.

* * * * *